United States Patent
Kiyonaka et al.

(10) Patent No.: US 7,867,516 B2
(45) Date of Patent: Jan. 11, 2011

(54) MEDICINAL PREPARATION CONTAINING 5-METHYL-1-PHENYL-2-(1H)-PYRIDONE AS ACTIVE INGREDIENT

(75) Inventors: Gakuji Kiyonaka, Amagasaki (JP); Yoshihiro Furuya, Amagasaki (JP); Yusuke Suzuki, Settsu (JP)

(73) Assignee: Shionogi & Co., Ltd., Osaka-shi (JP)

( * ) Notice: Subject to any disclaimer, the term of this patent is extended or adjusted under 35 U.S.C. 154(b) by 685 days.

(21) Appl. No.: 10/470,334

(22) PCT Filed: Jan. 25, 2002

(86) PCT No.: PCT/JP02/00544

§ 371 (c)(1), (2), (4) Date: Jul. 28, 2003

(87) PCT Pub. No.: WO02/060446

PCT Pub. Date: Aug. 8, 2002

(65) Prior Publication Data

US 2004/0048902 A1    Mar. 11, 2004

(30) Foreign Application Priority Data

Jan. 29, 2001    (JP) .............................. 2001-019393

(51) Int. Cl.
*A61K 9/28* (2006.01)
*A61K 9/36* (2006.01)

(52) U.S. Cl. ........................ 424/474; 424/464; 424/465; 424/480

(58) Field of Classification Search ................. 424/435, 424/464, 465, 488, 467, 486
See application file for complete search history.

(56) References Cited

U.S. PATENT DOCUMENTS

| | | | | |
|---|---|---|---|---|
| 3,974,281 A | * | 8/1976 | Gadekar | ..................... 514/345 |
| 4,042,699 A | | 8/1977 | Gadekar | |
| 4,052,509 A | | 10/1977 | Gadekar | |
| 5,271,946 A | * | 12/1993 | Hettche | ..................... 424/490 |
| 5,681,382 A | | 10/1997 | Kokubo | |
| 6,299,904 B1 | * | 10/2001 | Shimizu et al. | ............. 424/464 |
| 6,328,994 B1 | * | 12/2001 | Shimizu et al. | ............. 424/489 |

FOREIGN PATENT DOCUMENTS

| | | |
|---|---|---|
| EP | 0 383 591 | 8/1990 |
| EP | 0 901 787 A1 * | 9/1998 |
| EP | 0 901 787 A1 | 3/1999 |
| EP | 1 319 409 A1 | 6/2003 |
| WO | WO 90/09176 | 8/1990 |
| WO | WO 94/26249 | 11/1994 |
| WO | WO 97/10712 | 3/1997 |
| WO | WO 97/41830 | 11/1997 |

* cited by examiner

*Primary Examiner*—Michael G Hartley
*Assistant Examiner*—Micah-Paul Young
(74) *Attorney, Agent, or Firm*—Finnegan, Henderson, Farabow, Garrett & Dunner, LLP

(57) ABSTRACT

A tablet characterized by comprising 5-methyl-1-phenyl-2-(1H)-pyridone as the main ingredient and, based on the main ingredient, 10 to 50 wt. % excipient, 5 to 40 wt. % disintegrator, 1 to 10 wt. % binder, 0.5 to 5 wt. % lubricant, 2 to 6 wt. % coating basis, and 0.05 to 3 wt. % light-shielding agent, wherein the odor or bitterness of the 5-methyl-1-phenyl-2-(1H)-pyridone is masked and the light stability is improved.

1 Claim, No Drawings

MEDICINAL PREPARATION CONTAINING 5-METHYL-1-PHENYL-2-(1H)-PYRIDONE AS ACTIVE INGREDIENT

TECHNICAL FIELD

The present invention relates to a tablet containing as the main ingredient 5-methyl-1-phenyl-2-(1H)-pyridone.

BACKGROUND ART

5-Methyl-1-phenyl-2-(1H)-pyridone (nonproprietary name: pirfenidone) is a medicine for pulmonary fibrosis as indication. Various effects of pirfenidone have been reported, for example, 1) treating effect for fibrosis in lung, arteriosclerotic lesion, or the like is described in JP Laid-Open (Tokukai) No. H02-215719, 2) a similar effect to 1) of pirfenidone analogs is described in JP Laid-Open (Tokuhyo) No. H08-510251, 3) usefulness for treating inflammation in respiratory organs or cutis is described in U.S. Pat. No. 3,974,281, U.S. Pat. No. 4,042,699, and U.S. Pat. No. 4,052,509, and 4) inhibiting effect to the synthesis and release of TNF-α is described in JP Laid-Open (Tokuhyo) No. H11-512699.

In the above-mentioned 1) and 2), exemplified as a dosage form of pirfenidone are capsule, tablet, powder, granule, syrup, injection, cream, ointment, insufflation, eye lotion, suppository, and pill, preferable is capsule, injection, cream, and ointment, and working examples are only capsule and ointment. A tablet of pirfenidone and its preparation are not described concretely.

With regard to the dosage of pirfenidone, 600 mg to 2400 mg is administrated three times a day in above-mentioned 1). In test example 1 of 2), capsule containing 800 mg, 1200 mg, and 1600 mg of pirfenidone are described. In order to obtain a sufficient therapeutic effect, pirfenidone must be administrated much higher dose in comparison with a usual medicine.

In general, there are eight types of capsule: No. 000, 00, 0, 1, 2, 3, 4, and 5. The bigger the number is, the smaller the size is. The general amount of a medicine contained in each capsule depending on the bulk density or compressibility of the medicine, as follows: about 60 mg to 100 mg in No. 5 capsule, about 100 mg to 170 mg in No. 4 capsule, about 140 mg to 220 mg in No. 3 capsule, about 180 mg to 300 mg in No. 2 capsule, about 240 mg to 390 mg in No. 1 capsule, and about 340 mg to 540 mg in No. 0 capsule. While No. 2 to No. 4 capsules have often been used for administration to human, a smaller types such as No. 3 to No. 5 capsules are becoming more popular in light of easy administration. A capsule usually contains not only an active ingredient, but also a pharmaceutical additive such as excipient, binder, and disintegrator, for improving the stability and efficacy of the active ingredient.

For example, if the amount of pirfenidone per one dose is 600 mg as mentioned above, amount of granules or mixed powder of pirfenidone to be filled in a capsule is about 800 mg to 850 mg. In encapsulating such an amount a No. 000 capsule or two No. 0 capsules are needed, and a patient has a strong pain during the administration. In case of much higher dose, it is impossible to prepare a practical capsule

DISCLOSURE OF INVENTION

In General, a tablet is readily orally administrated than a capsule. The present inventors investigated a formulating of pirfenidone into a tablet which is considered to be effective to improve the compliance in oral administration of a high dose of pirfenidone. In the process, problems were found such as 1) a characteristic odor or bitterness of pirfenidone, 2) low compressibility of pirfenidone itself, and 3) light-stability.

In the above situation, the inventors of the present invention have prepared a pirfenidone tablet improved for the compliance, which masks its odor or bitterness, and has the light-stability and rapid dissolution rate, being compact and of sufficient hardness in spite of high content of the main ingredient, whereby accomplished the present invention.

That is, the present invention relates to the following.

1) A tablet containing as the main ingredient 5-methyl-1-phenyl-2-(1H)-pyridone.

2) A tablet as described in 1), the weight of which is 100 to 1000 mg.

3) A tablet as described in 1) or 2), which contains 10 to 85 wt. % the main ingredient to the weight of the tablet.

4) A tablet as described in any one of 1) to 3), wherein the content of the main ingredient is 200 mg to 400 mg.

5) A tablet as described in any one of 1) to 4), which contains a light-shielding agent.

6) A tablet as described in 5), which contains a 0.05 to 3 wt. % of the shielding agent based on the main ingredient.

7) A tablet as described in any one of 1) to 4), which contains 10 to 50 wt. % excipient, 5 to 40 wt. % disintegrator, 1 to 10 wt. % binder, 0.5 to 5 wt. % lubricant, 2 to 6 wt. % coating basis, and 0.05 to 3 wt. % light-shielding agent based on the main ingredient.

8) A tablet as described in 7), which contains 0.01 to 1 wt. % plasticizer based on the main ingredient.

9) A tablet as described in any one of 1) to 4), which consists of a plain tablet containing 10 to 50 wt. % excipient, 5 to 40 wt. % disintegrator, 1 to 10 wt. % binder, and 0.5 to 5 wt. % lubricant on the main ingredient, and coating layer containing 2 to 6 wt. % coating basis and 0.05 to 3 wt. % light-shielding agent based on the main ingredient.

10) A tablet as described in 9), which contains 0.01 to 1 wt. % plasticizer based on the main ingredient in a coating layer.

11) A tablet as described in any one of 1) to 4), which consists of a plain tablet containing 10 to 50 wt. % excipient selected from the group of lactose, corn starch, and crystalline cellulose, 5 to 40 wt. % disintegrator selected from the group of carmellose calcium, low substituted hydroxypropylcellulose, and cross-linked polyvinylpyrrolidone, 1 to 10 wt. % binder selected from the group of hydroxypropylcellulose and polyvinylpyrrolidone, and 0.5 to 5 wt. % lubricant selected from the group of magnesium stearate and talc on the main ingredient, and a coating layer containing 2 to 6 wt. % coating basis selected from the group of hydroxypropylmethylcellulose and hydroxypropylcellulose, 0.01 to 1 wt. % plasticizer selected from the group of triethyl citrate and triacetin, and 0.05 to 3 wt. % light-shielding agent selected from the group of titanium oxide and ferric oxide based on the main ingredient.

12) A tablet as described in 11), which consists of a plain tablet containing 10 to 50 wt. % lactose, 5 to 40 wt. % carmellose calcium, 1 to 10 wt. % hydroxypropylcellulose, and 0.5 to 5 wt. % magnesium stearate on the main ingredient, and a coating layer containing 2 to 6 wt. % hydroxypropylmethylcellulose, 0.01 to 1 wt. % triethyl citrate and 0.05 to 3 wt. % titanium oxide based on the main ingredient.

13) A tablet as described in any one of 1) to 4), which consists of a plain tablet containing 20 to 30 wt. % excipient selected from the group of lactose, corn starch, and crystalline cellulose, 7.5 to 15 wt. % disintegrator selected from the group of carmellose calcium, low substituted hydroxypropylcellulose, and cross-linked polyvinylpyrrolidone, 2 to 5 wt. % binder selected from the group of hydroxypropylcellulose and polyvinylpyrrolidone, and 0.5 to 3 wt. % lubricant selected from the group of magnesium stearate and talc on the main ingredient, and a coating layer containing 2 to 4 wt. % coating basis selected from the group of hydroxypropylmethylcellulose and hydroxypropylcellulose, 0.01 to 1 wt. % plasticizer selected from the group of triethyl citrate and triacetin, and 0.8 to 3 wt. % titanium oxide as a light-shielding agent based on the main ingredient.

14) A tablet as described in 13), which consists of a plain tablet containing 20 to 30 wt. % lactose, 7.5 to 15 wt. % carmellose calcium, 2 to 5 wt. % hydroxypropylcellulose, and 0.5 to 3 wt. magnesium stearate on the main ingredient, and a coating layer containing 2 to 4 wt. % hydroxypropylmethylcellulose, 0.01 to 1 wt. % triethyl citrate and 0.8 to 3 wt. % titanium oxide based on the main ingredient.

In the present specification, the term "excipient" means an excipient used in usual pharmaceutical preparations. Examples of the excipient include silicic acids such as light anhydrous silicic acid, synthetic aluminum silicate, and magnesium aluminometasilicate, inorganic salts such as calcium phosphate, calcium carbonate, and calcium sulfate, sugars such as lactose, sucrose, dextrose, mannitol, and sorbitol, starches such as corn starch, α starch, carboxymethyl starch, celluloses such as crystalline cellulose, and low substituted hydroxypropylcellulose, gum Arabic, dextran and pullulan. Lactose, corn starch, and crystalline cellulose are more preferable.

In the present specification, the term "disintegrator" means an additive agent which is used in order to disintegrate and disperse a tablet to minute particles t in the digestive organ. Examples of the disintegrator include corn starch, carboxymethylcellulose, carboxymethylcellulose calcium, low substituted hydroxypropylcellulose, carmellose sodium, crosscarmellose sodium, carboxymethylstarch sodium, and cross-linked polyvinylpyrrolidone. Carmellose calcium, low substituted hydroxypropylcellulose, cross-linked polyvinylpyrrolidone, and the like are more preferable.

In the present specification, the term "binder" means a binder used in usual pharmaceutical preparations. Examples of the binder include hydroxypropylcellulose, hydroxypropylmethylcellulose, and methylcellulose, polyvinylpyrrolidone. Hydroxypropylcellulose, polyvinylpyrrolidone, and the like are more preferable.

In the present specification, as "lubricant" are exemplified talc, calcium stearate, sodium stearate, and magnesium stearate. Magnesium stearate, talc, and the like are more preferable.

In the present specification, as "coating basis" are exemplified sucrose, talc, precipitated calcium carbonate, gelatin, gum Arabic, pullulan, hydroxypropylcellulose, hydroxypropylmethylcellulose, polyvinylacetal diethylaminoacetate, aminoalkyl methacrylate copolymer, cellulose acetate phthalate, methacrylic acid copolymer L, methacrylic acid copolymer LD, methacrylic acid copolymer S, hydroxypropylmethylcellulose phthalate, hydroxymethylpropylmethylcellulose acetate succinate, and carboxymethylethylcellulose. Hydroxypropylmethylcellulose, hydroxypropylcellulose, and the like are more preferable.

In the present specification, the term "light-shielding agent" means a light-shielding agent used in usual pharmaceutical preparations. Examples of the light-shielding agent include titanium oxide and ferric oxide. Titanium oxide, and the like are more preferable.

In the present specification, the term "plasticizer" means a plasticizer used in usual pharmaceutical preparations. Examples of the plasticizer include triethyl citrate, triacetin, glycerin fatty acid ester, and phthalic acid ester. Triethyl citrate, triacetin, and the like are more preferable.

BEST MODE FOR CARRYING OUT THE INVENTION

The present invention tablet is prepared in the following A) to D) processes.

A) A mixed powder containing pirfenidone, an excipient, and a disintegrator is granulated by spraying a binder with a fluid bed granulator to give granules.

B) The obtained granules are mixed with a disintegrator, a lubricant, and the like and is compressed at a force of 8 to 18 kN, preferably 11 to 15 kN to give pirfenidone plain tablets.

C) A coating solution containing a coating basis, a plasticizer (if necessary), and a light-shielding agent etc. is prepared.

D) The target pirfenidone tablet is obtained by coating the pirfenidone plain tablet obtained in B) with the above-mentioned coating solution.

In the above-mentioned processes, additives used in a usual solid preparation may be added appropriately.

The present invention relates to a tablet containing 5-methyl-1-phenyl-2-(1H)-pyridone as the main ingredient and preferable is a 100 to 1000 mg weight of tablet. 150 to 700 mg is more preferable and 240 to 480 mg is the most preferable. The amount of the active ingredient is preferably 10 to 85 wt. % the main ingredient to the tablet. 25 to 85 wt. % is more preferable and 50 to 85 wt. % is the most preferable. It is preferable that the content of the main ingredient is 200 mg to 400 mg.

The designed tablet is more compact, easier to take and contains a more amount of the main ingredient than capsule, thus effectively exhibiting the efficacy.

That is, the present invention tablet includes a more compact tablet than a capsule containing 5-methyl-1-phenyl-2-(1H)-pyridone as the main ingredient.

Further the present inventors have discovered the problem of light-stability of pirfenidone tablet in the preparation, and found a pirfenidone tablet improving the light-stability with a light-shielding agent. Furthermore, they found preferable are a tablet including 0.05 to 3 wt. % light-shielding agent and a tablet including a light-shielding agent in the coating layer.

That is, the present invention tablet includes a tablet improving the light-stability and containing 5-methyl-1-phenyl-2-(1H)-pyridone as the main ingredient.

Preferable amounts of respective components except the main ingredient in a plain tablet are shown by wt. % to pirfenidone as the main ingredient. In consideration of the compliance, it is preferable that the amount of the other components is as small as possible because the amount of pirfenidone as the main ingredient is much. But the hardness of a tablet may decrease if the amounts of the other components are too little. An excipient is preferably a) 10 to 50 wt. %. b) 15 to 40 wt. % is more preferable. c) 20 to 30 wt. % is the most preferable. A disintegrator is preferably d) 5 to 40 wt. %. e) 5 to 25 wt. % is more preferable. f) 7.5 to 15 wt. % is the most preferable. A binder is preferably g) 1 to 10 wt. %. h) 1 to 7.5 wt. % is more preferable. i) 2 to 5 wt. % is the most preferable. A lubricant is preferably j) 0.5 to 5 wt. %. k) 0.5 to 4 wt. % is more preferable. l) 0.5 to 3 wt. % is the most preferable.

Preferable amounts of respective components in a coating solution are shown by wt. % to pirfenidone as the main ingredient. The components include a coating basis in order to mask a characteristic odor or bitter of pirfenidone, and a light-shielding agent to improve the light-stability, preferably that the amounts of while are as small as possible like the plain tablet. A coating basis is preferably m) 2 to 6 wt. %. n) 2 to 5 wt. % is more preferable. o) 2 to 4 wt. % is the most preferable. A light-shielding agent is preferably p) 0.05 to 3 wt. %. q) 0.05 to 2 wt. % is more preferable. r) 0.8 to 1.5 wt. % is the most preferable. A plasticizer is preferably s) not included or t) 0.05 to 1 wt. % if included.

Preferable amounts of the above-mentioned components to pirfenidone in the present invention tablet are shown as follows. That is, (excipient, disintegrator, binder, lubricant, coating basis, light-shielding agent, plasticizer)=(a, d, g, j, m, p, s), (a, d, g, j, m, p, t), (a, d, g, j, m, q, s), (a, d, g, j, m, q, t), (a, d, g, j, m, r, s), (a, d, g, j, m, r, t), (a, d, g, j, n, p, s), (a, d, g, j, n, p, t), (a, d, g, j, n, q, s), (a, d, g, j, n, q, t), (a, d, g, j, n, r, s), (a, d, g, j, n, r, t), (a, d, g, j, o, p, s), (a, d, g, j, o, p, t), (a, d, g, j, o, q, s), (a, d, g, j, o, q, t), (a, d, g, j, o, r, s), (a, d, g, j, o, r, t), (a, d, g, k, m, p, s), (a, d, g, k, m, p, t), (a, d, g, k, m, q, s), (a, d, g, k, m, q, t), (a, d, g, k, m, r, s), (a, d, g, k, m, r, t), (a, d, g, k, n, p, s), (a, d, g, k, n, p, t), (a, d, g, k, n, q, s), (a, d, g, k, n, q, t), (a, d, g, k, n, r, s), (a, d, g, k, n, r, t), (a, d, g, k, o, p, s), (a, d, g, k, o, p, t), (a, d, g, k, o, q, s), (a, d, g, k, o, q, t), (a, d, g, k, o, r, s), (a, d, g, k, o, r, t), (a, d, g, l, m, p, s), (a, d, g, l, m, p, t), (a, d, g, l, m, q, s), (a, d, g, l, m, q, t), (a, d, g, l, m, r, s), (a, d, g, l, m, r, t), (a, d, g, l, n, p, s), (a, d, g, l, n, p, t), (a, d, g, l, n, q, s), (a, d, g, l, n, q, t), (a, d, g, l, n, r, s), (a, d, g, l, n, r, t), (a, d, g, l, o, p, s), (a, d, g, l, o, p, t), (a, d, g, l, o, q, s), (a, d, g, l, o, q, t), (a, d, g, l, o, r, s), (a, d, g, l, o, r, t), (a, d, h, j, m, p, s), (a, d, h, j, m, p, t), (a, d, h, j, m, q, s), (a, d, h, j, m, q, t), (a, d, h, j, m, r, s), (a, d, h, j, m, r, t), (a, d, h, j, n, p, s), (a, d, h, j, n, p, t), (a, d, h, j, n, q, s), (a, d, h, j, n, q, t), (a, d, h, j, n, r, s), (a, d, h, j, n, r, t), (a, d, h, j, o, p, s), (a, d, h, j, o, p, t), (a, d, h, j, o, q, s), (a, d, h, j, o, q, t), (a, d, h, j, o, r, s), (a, d, h, j, o, r, t), (a, d, h, k, m, p, s), (a, d, h, k, m, p, t), (a, d, h, k, m, q, s), (a, d, h, k, m, q, t), (a, d, h, k, m, r, s), (a, d, h, k, m, r, t), (a, d, h, k, n, p, s), (a, d, h, k, n, p, t), (a, d, h, k, n, q, s), (a, d, h, k, n, q, t), (a, d, h, k, n, r, s), (a, d, h, k, n, r, t), (a, d, h, k, o, p, s), (a, d, h, k, o, p, t), (a, d, h, k, o, q, s), (a, d, h, k, o, q, t), (a, d, h, k, o, r, s), (a, d, h, k, o, r, t), (a, d, h, l, m, p, s), (a, d, h, l, m, p, t), (a, d, h, l, m, q, s), (a, d, h, l, m, q, t), (a, d, h, l, m, r, s), (a, d, h, l, m, r, t), (a, d, h, l, n, p, s), (a, d, h, l, n, p, t), (a, d, h, l, n, q, s), (a, d, h, l, n, q, t), (a, d, h, l, r, s), (a, d, h, l, n, r, t), (a, d, h, l, o, p, s), (a, d, h, l, o, p, t), (a, d, h, l, o, q, s), (a, d, h, l, o, q, t), (a, d, h, l, o, r, s), (a, d, h, l, o, r, t), (a, d, i, j, m, p, s), (a, d, i, j, m, p, t), (a, d, i, j, m, q, s), (a, d, i, j, m, q, t), (a, d, i, j, m, r, s), (a, d, i, j, m, r, t), (a, d, i, j, n, p, s), (a, d, i, j, n, p, t), (a, d, i, j, n, q, s), (a, d, i, j, n, q, t), (a, d, i, j, a, r, s), (a, d, i, j, n, r, t), (a, d, i, j, o, p, s), (a, d, i, j, o, p, t), (a, d, h, j, o, q, s), (a, d, h, j, o, q, t), (a, d, i, j, o, r, s), (a, d, i, j, o, r, t), (a, d, i, k, m, p, s), (a, d, i, k, m, p, t), (a, d, i, k, m, q, s), (a, d, i, k, m, q, t), (a, d, i, k, m, r, s), (a, d, i, k, m, r, l), (a, d, i, k, n, p, s), (a, d, i, k, n, p, t), (a, d, i, k, n, q, s), (a, d, i, k, n, q, t), (a, d, i, k, n, r, s), (a, d, i, k, n, r, t), (a, d, i, k, o, p, s), (a, d, i, k, o, p, t), (a, d, i, k, o, q, s), (a, d, i, k, o, q, t), (a, d, i, k, o, r, s), (a, d, i, k, o, r, t), (a, d, i, l, m, p, s), (a, d, i, l, m, p, t), (a, d, i, l, m, q, s), (a, d, i, l, m, q, t), (a, d, i, l, m, r, s), (a, d, i, l, m, r, t), (a, d, i, l, n, p, s), (a, d, i, l, n, p, t), (a, d, i, l, n, q, s), (a, d, i, 1, n, q, t), (a, d, i, l, n, r, s), (a, d, i, l, n, r, t), (a, d, i, l, o, p, s), (a, d, i, l, o, p, t), (a, d, i, l, o, q, s), (a, d, i, l, o, q, t), (a, d, i, l, o, r, s), (a, d, i, l, o, r, t), (a, e, g, j, m, p, s), (a, e, g, j, m, p, t), (a, e, g, j, m, q, s), (a, e, g, j, m, q, t), (a, e, g, j, m, r, s), (a, e, g, j, m, r, t), (a, e, g, j, n, p, s), (a, e, g, j, n, p, t), (a, e, g, j, n, q, s), (a, e, g, j, n, q, t), (a, e, g, j, n, r, s), (a, e, g, j, n, r, t), (a, e, g, j, o, p, s), (a, e, g, j, o, p, t), (a, e, g, j, o, q, s), (a, e, g, j, o, q, t), (a, e, g, j, o, r, s), (a, e, g, j, o, r, t), (a, e, g, k, m, p, s), (a, e, g, k, m, p, t), (a, e, g, k, m, q, s), (a, e, g, k, m, q, t), (a, e, g, k, m, r, s), (a, e, g, k, m, r, t), (a, e, g, k, n, p, s), (a, e, g, k, n, p, t), (a, e, g, k, n, q, s), (a, e, g, k, n, q, t), (a, e, g, k, n, r, s), (a, e, g, k, n, r, t), (a, e, g, k, o, p, s), (a, e, g, k, o, p, t), (a, e, g, k, o, q, s), (a, e, g, k, o, q, t), (a, e, g, k, o, r, s), (a, e, g, k, o, r, t), (a, e, g, l, m, p, s), (a, e, g, l, m, p, t), (a, e, g, l, m, q, s), (a, e, g, l, m, q, t), (a, e, g, l, m, r, s), (a, e, g, l, m, r, t), (a, e, g, l, n, p, s), (a, e, g, l, n, p, t), (a, e, g, l, n, q, s), (a, e, g, l, n, q, t), (a, e, g, l, n, r, s), (a, e, g, l, n, r, t), (a, e, g, l, o, p, s), (a, e, g, l, o, p, t), (a, e, g, l, o, q, s), (a, e, g, l, o, q, t), (a, e, g, l, o, r, s), (a, e, g, l, o, r, t), (a, e, h, j, m, p, s), (a, e, h, j, m, p, t), (a, e, h, j, m, q, s), (a, e, h, j, m, q, t), (a, e, h, j, m, r, s), (a, e, h, j, m, r, t), (a, e, h, j, n, p, s), (a, e, h, j, n, p, t), (a, e, h, j, n, q, s), (a, e, h, j, n, q, t), (a, e, h, j, n, r, s), (a, e, h, j, n, r, t), (a, e, h, j, o, p, s), (a, e, h, j, o, p, t), (a, e, h, j, o, q, s), (a, e, h, j, o, q, t), (a, e, h, j, o, r, s), (a, e, h, j, o, r, t), (a, e, h, k, m, p, s), (a, e, h, k, m, p, t), (a, e, h, k, m, q, s), (a, e, h, k, m, q, t), (a, e, h, k, m, r, s), (a, e, h, k, m, r, t), (a, e, h, k, n, p, s), (a, e, h, k, n, p, t), (a, e, h, k, n, q, s), (a, e, h, k, n, q, t), (a, e, h, k, n, r, s), (a, e, h, k, n, r, t), (a, e, h, k, o, p, s), (a, e, h, k, o, p, t), (a, e, h, k, o, q, s), (a, e, h, k, o, q, t), (a, e, h, k, o, r, s), (a, e, h, k, o, r, t), (a, e, h, l, m, p, s), (a, e, h, l, m, p, t), (a, e, h, l, m, q, s), (a, e, h, l, m, q, t), (a, e, h, l, m, r, s), (a, e, h, l, m, r, t), (a, e, h, l, n, p, s), (a, e, h, l, n, p, t), (a, e, h, l, n, q, s), (a, e, h, l, n, q, t), (a, e, h, l, n, r, s), (a, e, h, l, n, r, t), (a, e, h, l, o, p, s), (a, e, h, l, o, p, t), (a, e, h, l, o, q, s), (a, e, h, l, o, q, t), (a, e, h, l, o, r, s), (a, e, h, l, o, r, t), (a, e, i, j, m, p, s), (a, e, i, j, m, p, t), (a, e, i, j, m, q, s), (a, e, i, j, m, q, t), (a, e, i, j, m, r, s), (a, e, i, j, m, r, t), (a, e, i, j, n, p, s), (a, e, i, j, n, p, t), (a, e, i, j, n, q, s), (a, e, i, j, n, q, t), (a, e, i, j, n, r, s), (a, e, i, j, n, r, t), (a, e, i, j, o, p, s), (a, e, i, j, o, p, t), (a, e, i, j, o, q, s), (a, e, i, j, o, q, t), (a, e, i, j, o, r, s), (a, e, i, j, o, r, t), (a, e, i, k, m, p, s), (a, e, i, k, m, p, t), (a, e, i, k, m, q, s), (a, e, i, k, m, q, t), (a, e, i, k, m, r, s), (a, e, i, k, m, r, t), (a, e, i, k, n, p, s), (a, e, i, k, n, p, t), (a, e, i, k, n, q, s), (a, e, i, k, n, q, t), (a, e, i, k, n, r, s), (a, e, i, k, n, r, t), (a, e, i, k, o, p, s), (a, e, i, k, o, p, t), (a, e, i, k, o, q, s), (a, e, i, k, o, q, t), (a, e, i, k, o, r, s), (a, e, i, k, o, r, t), (a, e, i, l, m, p, s), (a, e, i, l, m, p, t), (a, e, i, l, m, q, s), (a, e, i, l, m, q, t), (a, e, i, l, m, r, s), (a, e, i, l, m, r, t), (a, e, i, l, n, p, s), (a, e, i, l, n, p, t), (a, e, i, l, n, q, s), (a, e, i, l, n, q, t), (a, e, i, l, n, r, s), (a, e, i, l, n, r, t), (a, e, i, l, o, p, s), (a, e, i, l, o, p, t), (a, e, i, l, o, q, s), (a, e, i, l, o, q, t), (a, e, i, l, o, r, s), (a, e, i, l, o, r, t), (a, f, g, j, m, p, s), (a, f, g, j, m, p, t), (a, f, g, j, m, q, s), (a, f, g, j, m, q, t), (a, f, g, j, m, r, s), (a, f, g, j, m, r, t), (a, f, g, j, n, p, s), (a, f, g, j, n, p, t), (a, f, g, j, n, q, s), (a, f, g, j, n, q, t), (a, f, g, j, n, r, s), (a, f, g, j, n, r, t), (a, f, g, j, o, p, s), (a, f, g, j, o, p, t), (a, f, g, j, o, q, s), (a, f, g, j, o, q, t), (a, f, g, j, o, r, s), (a, f, g, j, o, r, t), (a, f, g, k, m, p, s), (a, f, g, k, m, p, t), (a, f, g, k, m, q, s), (a, f, g, k, m, q, t), (a, f, g, k, m, r, s), (a, f, g, k, m, r, t), (a, f, g, k, n, p, s), (a, f, g, k, n, p, t), (a, f, g, k, n, q, s), (a, f, g, k, n, q, t), (a, f, g, k, n, r, s), (a, f, g, k, n, r, t), (a, f, g, k, o, p, s), (a, f, g, k, o, p, t), (a, f, g, k, o, q, s), (a, f, g, k, o, q, t), (a, f, g, k, o, r, s), (a, f, g, k, o, r, t), (a, f, g, l, m, p, s), (a, f, g, l, m, p, t), (a, f, g, l, m, q, s), (a, f, g, l, m, q, t), (a, f, g, l, m, r, s), (a, f, g, l, m, r, t), (a, f, g, l, n, p, s), (a, f, g, l, n, p, t), (a, f, g, l, n, q, s), (a, f, g, l, n, q, t), (a, f, g, l, n, r, s), (a, f, g, l, n, r, t) (a, f, g, l, o, p, s), (a, f, g, l, o, p, t), (a, f, g, l, o, q, s), (a, f, g, l, o, q, t), (a, f, g, l, o, r, s), (a, f, g, l, o, r, t), (a, f, h, j, m, p, s), (a, f, h, j, m, p, t), (a, f, h, j, m, q, s), (a, f, h, j, m, q, t), (a, f, h, j, m, r, s), (a, f, h, j, m, r, t), (a, f, h, j, n, p, s), (a, f, h, j, n, p, t), (a, f, h, j, n, q, s), (a, f, h, j, n, q, t), (a, f, h, j, n, r, s), (a, f, h, j, n, r, t), (a, f, h, j, o, p, s), (a, f, h, j, o, p, t), (a, f, h, j, o, q, s), (a, f, h, j, o, q, t), (a, f, h, j, o, r, s), (a, f, h, j, o, r, t), (a, f, h, k, m, p, s), (a, f, h, k, m, p, t), (a, f, h, k, m, q, s), (a, f, h, k, m, q, t), (a, f, h, k, m, r, s), (a, f, h, k, m, r, t), (a, f, h, k, n, p, s), (a, f, h, k, n, p, t), (a, f, h, k, n, q, s), (a, f, h, k, n, q, t), (a, f, h, k, n, r, s), (a, f, h, k, n, r, t), (a, f, h, k, o, p, s), (a, f, h, k, o, p, t), (a, f, h, k, o, q, s), (a, f, h, k, o, q, s) (a, f, h, k, o, r, s), (a, f, h, k, o, r, t), (a, f, h, l, m, p, s), (a, f, h, l, m, p, t), (a, f, h, l m, q, s), (a, f, h, l, m q, t), (a, f, h, l, m, r, s), (a, f, h, l, m, r, t), (a, f, h, l, n, p, s), (a, f, h, l, n, p, t), (a, f h, l, n, q, s), (a, f, h, l, n, q, t), (a, f, h, l, n, r, s), (a, f, h, l, n, r, t), (a, f, h, l, o, p, s), (a, f, h, l, o, p, t), (a, f, h, l, o, q, s), (a, f, h, l, o, q, t), (a, f, h, l, o, r, s), (a, f, h, l, o, r, t), (a, f, i, j, m, p, s), (a, f, i, j, n, p, t), (a, f, l, j, m, q, s), (a, f, l, j, m, q, t), (a, f, i, j, m, r, s), (a, f, i, j, m, r, t), (a, f, i, j, n, p, s), (a, f, i, j, n, p, s) (a, f, i, j, n, q, s), (a, f, i, j, n, q, t), (a, f, i, j, n, r, s), (a, f, i, j, n, r, t), (a, f, i, j, o, p, s), (a, f, l, j, o, p, t), (a, f, i, j, o, q, s), (a, f, i, j, o, q, t), (a, f, i, j, o, r, s), (a, f, i, j, o, r, t), (a, f, i, k, m, p, s), (a, f, i, k, m, p, s) (a, f, i, k, m, q, s), (a, f, i, k, m, q, t), (a, f, i, k, m, r, s), (a, f, i, k, m, r, t), (a, f, i, k, n, p, s), (a, f, i, k, n, p, t), (a, f, i, k, n, q, s), (a, f, i, k, n, q, t), (a, f, i, k, n, r, s), (a, f, i, k, n, r, t), (a, f, i, k, o, p, s), (a, f, i, k, o, p, t), (a, f, i, k, o, q, s), (a, f, i, k, o, q, t), (a, f, i, k, o, r, s), (a, f, i, k, o, r, t), (a, f, i, l, m, p, s), (a, f, i, l, m, p, t), (a, f, i, l, m, q, s), (a, f, i, l, m, q, t), (a, f, i, m, r, s), (a, f, i, l, m, r, t), (a, f, i, l, n, p, s), (a, f, i, l, n, p, t), (a, f, i, l, n, q, s), (a, f, i, l, n, q, t), (a, f, i, l, n, r, s), (a, f, i, l, n, r, t), (a, f, i, l, o, p, s), (a, f, i, l, o, p, t), (a, f, i, l, o, q, s), (a, f, i, l, o, q, t), (a, f, i, l, o, r, s), (a, f, i, l, o, r, t), (b, d, g, j, m, p, s), (b, d, g, j, m, p, t), (b, d, g, j, in, q, s), (b, d, g, j, m, q, t), (b, d, g, j, in, r, s), (b, d, g, j, m, r, t), (b, d, g, j, n, p, s), (b, d, g, j, n, p, t), (b, d, g, j, n, q, s), (b, d, g, j, n, q, t), (b, d, g, j, n, r, s), (b, d, g, j, n, r, t), (b, d, g, j, o, p, s), (b, d, g, j, o, p, t), (b, d, g, j, o, q, s), (b, d, g, j, o, q, t), (b, d, g, j, o, r, s), (b, d, g, j, o, r, t), (b, d, g, k, m, p, s), (b, d, g, k, m, p, t), (b, d, g, k, m, q, s), (b, d, g, k, m, q, t), (b, d, g, k, m, r, s), (b, d, g, k, m, r, t), (b, d, g, k, n, p, s), (b, d, g, k, n, p, t), (b, d, g, k, n, q, s), (b, d, g, k, n, q, t), (b, d, g, k, n, r, s), (b, d, g, k, n, r, t), (b, d, g, k, o, p, s), (b, d, g, k, o, p, t), (b, d, g, k, o, q, s), (b, d, g, k, o, q, t), (b, d, g, k, o, r, s), (b, d, g, k, o, r, t), (b, d, g, l, m, p, s), (b, d, g, l, m, p, t), (b, d, g, l, m, q, s), (b, d, g, l, m, q, t), (b, d, g, l, m, r, s), (b, d, g, l, m, r, t), (b, d, g, l, n, p, s), (b, d, g, l, n, p, t), (b, d, g, l, n, q, s), (b, d, g, l, n, q, t), (b, d, g, l, n, r, s), (b, d, g, l, n, r, t), (b, d, g, l, o, p, s), (b, d, g, l, o, p, t), (b, d, g, l, o, q, s), (b, d, g, l, o, q, t), (b, d, g, l, o, r, s), (b, d, g, l, o, r, t), (b, d, h, j, m, p, s), (b, d, h, j, m, p, t), (b, d, h, j, m, q, s), (b, d, h, j, m, q, t), (b, d, h, j, m, r, s), (b, d, h, j, m, r, t), (b, d, h, j, n, p, s), (b, d, h, j, n, p, t), (b, d, h, j, n, q, s), (b, d, h, j, n, q, t), (b, d, h, j, n, r, s), (b, d, h, j, n, r, t), (b, d, h, j, o, p, s), (b, d, h, j, o, p, t), (b, d, h, j, o, q, s), (b, d, h, j, o, q, t), (b, d, h, j, o, r, s), (b, d, h, j, o, r, t), (b, d, h, k, m, p, s), (b, d, h, k, m, p, t), (b, d, h, k, m, q, s), (b, d, h, k, m, q, t), (b, d, h, k, m, r, s), (b, d, h, k, m, r, t), (b, d, h, k, n, p, s), (b, d, h, k, n, p, t), (b, d, h, k, n, q, s), (b, d, h, k, n, q, t), (b, d, h, k, n, r, s), (b, d, h, k, n, r, t), (b, d, h, k, o, p, s), (b, d, h, k, o, p, t), (b, d, h, k, o, q, s), (b, d, h, k, o, q, t), (b, d, h, k, o, r, s), (b, d, h, k, o, r, t), (b, d, h, l, m, p, s), (b, d, h, l, m, p, t), (b, d, h, l, m, q, s), (b, d, h, l, m, q, t), (b, d, h, l, m, r, s), (b, d, h, l, m, r, t), (b, d, h, l, n, p, s), (b, d, h, l, n, p, t), (b, d, h, l, n, q, s), (b, d, h, l, n, q, t), (b, d, h, l, n, r, s), (b, d, h, l, n, r, t), (b, d, h, l, o, p, s), (b, d, h, l, o, p, t), (b, d, h, l, o, q, s), (b, d, h, l, o, q, t), (b, d, h, l, o, r, s), (b, d, h, l, o, r, t), (b, d, i, j, m, p, s), (b, d, i, j, m, p, t), (b, d, i, j, m, q, s), (b, d, i, j, m, q, t), (b, d, i, j, m, r, s), (b, d, i, j, m, r, t), (b, d, i, j, n, p, s), (b, d, i, j, n, p, t), (b, d, i, j, n, q, s), (b, d, i, j, n, q, t), (b, d, i, j, n, r, s), (b, d, i, j, n, r, t), (b, d, i, j, o, p, s), (b, d, i, j, o, p, t), (b, d, i, j, o, q, s), (b, d, i, j, o, q, t), (b, d, i, j, o, r, s), (b, d, i, j, o, r, t), (b, d, i, k, m, p, s), (b, d, i, k, m, p, t), (b, d, i, k, m, q, s), (b, d, i, k, m, q, t), (b, d, i, k, m, r, s), (b, d, i, k, m, r, t), (b, d, i, k, n, p, s), (b, d, i, k, n, p, t), (b, d, i, k, n, q, s), (b, d, i, k, n, q, t), (b, d, i, k, n, r, s), (b, d, i, k, n, r, t), (b, d, i, k, o, p, s), (b, d, i, k, o, p, t), (b, d, i, k, o, q, s), (b, d, i, k, o, q, t), (b, d, i, k, o, r, s), (b, d, i, k, o, r, t), (b, d, i, l, m, p, s), (b, d, i, l, m, p, t), (b, d, i, l, m, q, s), (b, d, i, l, m, q, t), (b, d, i, l, m, r, s), (b, d, i, l, m, r, t), (b, d, i, l, n, p, s), (b, d, i, l, n, p, t), (b, d, i, l, n, q, s), (b, d, i, l, n, q, t), (b, d, i, l, n, r, s), (b, d, i, l, n, r, t), (b, d, i, l, o, p, s), (b, d, i, l, o, p, t), (b, d, i, l, o, q, s), (b, d, i, l, o, q, t), (b, d, i, l, o, r, s), (b, d, i, l, o, r, t), (b, e, g, j, m, p, s), (b, e, g, j, m, p, t), (b, e, g, j, m, q, s), (b, e, g, j, m, q, t), (b, e, g, j, m, r, s), (b, e, g, j, m, r, t), (b, e, g, j, n, p, s), (b, e, g, j, n, p, t), (b, e, g, j, n, q, s), (b, e, g, j, n, q, t), (b, e, g, j, n, r, s), (b, e, g, j, n, r, t), (b, e, g, j, o, p, s), (b, e, g, j, o, p, t), (b, e, g, j, o, q, s), (b, e, g, j, o, q, t), (b, e, g, j, o, r, s), (b, e, g, j, o, r, t), (b, e, g, k, m, p, s), (b, e, g, k, m, p, t), (b, e, g, k, m, q, s), (b, e, g, k, m, q, t), (b, e, g, k, m, r, s), (b, e, g, k, m, r, t), (b, e, g, k, n, p, s), (b, e, g, k, n, p, t), (b, e, g, k, n, q, s), (b, e, g, k, n, q, t), (b, e, g, k, n, r, s), (b, e, g, k, n, r, t), (b, e, g, k, o, p, s), (b, e, g, k, o, p, t), (b, e, g, k, o, q, s), (b, e, g, k, o, q, t), (b, e, g, k, o, r, s), (b, e, g, k, o, r, t), (b, e, g, k, m, p, s), (b, e, g, l, m, p, t), (b, e, g, k, m, q, s), (b, e, g, k, m, q, t), (b, e, g, l, m, r, s), (b, e, g, l, m, r, t), (b, e, g, l, n, p, s), (b, e, g, l, n, p, t), (b, e, g, l, n, q, s), (b, e, g, l, n, q, t), (b, e, g, l, n, r, s), (b, e, g, l, n, r, t), (b, e, g, l, o, p, s), (b, e, g, l o, p, t), (b, e, g, l, o, q, s), (b, e, g, l, o, q, t), (b, e, g, l, o, r, s), (b, e, g, l, o, r, t), (b, e, h, j, m, p, s), (b, e, h, j, m, p, t), (b, e, h, j, m, q, s), (b, e, h, j, m, q, t), (b, e, h, j, m, r, s), (b, e, h, j, m, r, t), (b, e, h, j, n, p, s), (b, e, h, j, n, p, t), (b, e, h, j, n, q, s), (b, e, h, j, n, q, t), (b, e, h, j, n, r, s), (b, e, h, j, n, r, t), (b, e, h, j, o, p, s), (b, e, h, j, o, p, t), (b, e, h, j, o, q, s), (b, e, h, j, o, q, t), (b, e, h, j, o, r, s), (b, e, h, j, o, r, t), (b, e, h, k, m, p, s), (b, e, h, k, m, p, t), (b, e, h, k, m, q, s), (b, e, h, k, m, q, t), (b, e, h, k, m, r, s), (b, e, h, k, m, r, t), (b, e, h, k, n, p, s), (b, e, h, k, n, p, t), (b, e, h, k, n, q, s), (b, e, h, k, n, q, t), (b, e, h, k, n, r, s), (b, e, h, k, n, r, t), (b, e, h, k, o, p, s), (b, e, h, k, o, p, t), (b, e, h, k, o, q, s), (b, e, h, k, o, q, t), (b, e, h, k, o, r, s), (b, e, h, k, o, r, t), (b, e, h, l, m, p, s), (b, e, h, l, m, p, t), (b, e, h, l, m, q, s), (b, e, h, l, m, q, t), (b, e, b, l, m, r, s), (b, e, h, l, m, r, t), (b, e, h, l, n, p, s), (b, e, h, l, n, p, t), (b, e, h, l, n, q, s), (b, e, h, l, n, q, t), (b, e, h, l, n, r, s), (b, e, b, l, n, r, t), (b, e, h, l, o, p, s), (b, e, h, l, o, p, t), (b, e, h, l, o, q, s), (b, e, h, l, o, q, t), (b, e, h, l, o, r, s), (b, e, h, l, o, r, t), (b, e, i, j, m, p, s), (b, e, i, j, m, p, t), (b, e, i, j, m, q, s), (b, e, i, j, m, q, t), (b, e, i, j, m, r, s), (b, e, i, j, m, r, t), (b, e, i, j, n, p, s), (b, e, i, j, n, p, t), (b, e, i, j, n, q, s), (b, e, i, j, n, q, t), (b, e, i, j, n, r, s), (b, e, i, j, n, r, t), (b, e, i, j, o, p, s), (b, e, i, j, o, p, t), (b, e, i, j, o, q, s), (b, e, i, j, o, q, t), (b, e, i, j, o, r, s), (b, e, i, j, o, r, t), (b, e, i, k, m, p, s), (b, e, i, k, m, p, t), (b, e, i, k, m, q, s), (b, e, i, k, m, q, t), (b, e, i, k, m, r, s), (b, e, i, k, m, r, t), (b, e, i, k, n, p, s), (b, e, i, k, n, p, t), (b, e, i, k, n, q, s), (b, e, i, k, n, q, t), (b, e, i, k, n, r, s), (b, e, i, k, n, r, t), (b, e, i, k, o, p, s), (b, e, i, k, o, p, t), (b, e, i, k, o, q, s), (b, e, i, k, o, q, t), (b, e, i, k, o, r, s), (b, e, i, k, o, r, t), (b, e, i, l, m, p, s), (b, e, i, l, m, p, t), (b, e, i, l, m, q, s), (b, e, i, l, m, q, t), (b, e, i, l, m, r, s), (b, e, i, l, m, r, t), (b, e, i, l, n, p, s), (b, e, i, l, n, p, t), (b, e, i, I, n, q, s), (b, e, i, l, n, q, t), (b, e, i, l, n, r, s), (b, e, i, l, n, r, t), (b, e, i, l, o, p, s), (b, e, i, l, o, p, t), (b, e, i, l, o, q, s), (b, e, i, l, o, q, t), (b, e, i, l, o, r, s), (b, e, i, l, o, r, t), (b, f, g, j, m, p, s), (b, f, g, j, m, p, t), (b, f, g, j, m, q, s), (b, f, g, j, m, q, t), (b, f, g, j, m, r, s), (b, f, g, j, m, r, t), (b, f, g, j, n, p, s), (b, f, g, j, n, p, t), (b, f, g, j, n, q, s), (b, f, g, j, n, q, t), (b, f, g, j, n, r, s), (b, f, g, j, n, r, t), (b, f, g, j, o, p, s), (b, f, g, j, o, p, t), (b, f, g, j, o, q, s), (b, f, g, j, o, q, t), (b, f, g, j, o, r, s), (b, f, g, j, o, r, t), (b, f, g, k, m, p, s), (b, f, g, k, m, p, t), (b, f, g, k, m, q, s), (b, f, g, k, m, q, t), (b, f, g, k, m, r, s), (b, f, g, k, m, r, t), (b, f, g, k, n, p, s), (b, f, g, k, n, p, t), (b, f, g, k, n, q, s), (b, f, g, k, n, q, t), (b, f, g, k, n, r, s), (b, f, g, k, n, r, t), (b, f, g, k, o, p, s), (b, f, g, k, o, p, t), (b, f, g, k, o, q, s), (b, f, g, k, o, q, t), (b, f, g, k, o, r, s), (b, f, g, k, o, r, t), (b, f, g, l, m, p, s), (b, f, g, l, m, p, t), (b, f, g, l, m, q, s), (b, f, g, l, m, q, t), (b, f, g, l, m, r, s), (b, f, g, l, m, r, t), (b, f, g, l, n, p, s), (b, f, g, l, n, p, t), (b, f, g, l, n, q, s), (b, f, g, l, n, q, t), (b, f, g, l, n, r, s), (b, f, g, l, n, r, t), (b, f, g, l, o, p, s), (b, f, g, l, o, p, t), (b, f, g, l, o, q, s), (b, f, g, l, o, q, t), (b, f, g, l, o, r, s), (b, f, g, l, o, r, t), (b, f, h, j, m, p, s), (b, f, h, j, m, p, t), (b, f, h, j, m, q, s), (b, f, h, j, m, q, t), (b, f, h, j, m, r, s), (b, f, h, j, m, r, t), (b, f, h, j, n, p, s), (b, f, h, j, n, p, t), (b, f, h, j, n, q, s), (b, f, h, j, n, q, t), (b, f, h, j, n, r, s), (b, f, h, j, n, r, t), (b, f, h, j, o, p, s), (b, f, h, j, o, p, t), (b, f, h, j, o, q, s), (b, f, h, j, o, q, t), (b, f, h, j, o, r, s), (b, f, h, j, o, r, t), (b, f, h, k, m, p, s), (b, f, h, k, m, p, t), (b, f, h, k, m, q, s), (b, f, h, k, m, q, t), (b, f, h, k, m, r, s), (b, f, h, k, m, r, t), (b, f, h, k, n, p, s), (b, f, h, k, n, p, t), (b, f, h, k, n, q, s), (b, f, h, k, n, q, t), (b, f, h, k, n, r, s), (b, f, h, k, n, r, t), (b, f, h, k, o, p, s), (b, f, h, k, o, p, t), (b, f, h, k, o, q, s), (b, f, h, k, o, q, t), (b, f, h, k, o, r, s), (b, f, h, k, o, r, t), (b, f, h, l, m, p, s), (b, f, h, l, m, p, t), (b, f, h, l, m, q, s), (b, f, h, l, m, q, t), (b, f, h, l, m, r, s), (b, f, h, l, m, r, t), (b, f, h, l, n, p, s), (b, f, h, l, n, p, t), (b, f, h, l, n, q, s), (b, f, h, l, n, q, t), (b, f, h, l, n, r, s), (b, f, h, l, n, r, t), (b, f, h, l, o, p, s), (b, f, h, l, o, p, t), (b, f, h, l, o, q, s), (b, f, h, l, o, q, t), (b, f, h, l, o, r, s), (b, f, h, l, o, r, t), (b, f, i, j, m, p, s), (b, f, i, j, m, p, t), (b, f, i, j, m, q, s), (b, f, i, j, m, q, t), (b, f, i, j, m, r, s), (b, f, i, j, m, r, t), (b, f, i, j, n, p, s), (b, f, i, j, n, p, t), (b, f, i, j, n, q, s), (b, f, i, j, n, q, t), (b, f, i, j, n, r, s), (b, f, i, j, n, r, t), (b, f, i, j, o, p, s), (b, f, i, j, o, p, t), (b, f, i, j, o, q, s), (b, f, i, j, o, q, t), (b, f, i, j, o, r, s), (b, f, i, j, o, r, t), (b, f, i, k, m, p, s), (b, f, i, k, m, p, l), (b, f, i, k, m, q, s), (b, f, i, k, i, q, t), (b, f, i, k, m, r, s), (b, f, i, k, m, r, t), (b, f, i, k, n, p, s), (b, f, i, k, n, p, t), (b, f, i, k, n, q, s), (b, f, i, k, n, q, t), (b, f, i, k, n, r, s), (b, f, i, k, n, r, t), (b, f, i, k, o, p, s), (b, f, i, k, o, p, t), (b, f, i, k, o, q, s), (b, f, i, k, o, q, t), (b, f, i, k, o, r, s), (b, f, i, k, o, r, t), (b, f, i, l, m, p, s), (b, f, i, l, m, p, t), (b, f, i, l, m, q, s), (b, f, i, l, m, q, t), (b, f, i, l, m, r, s), (b, f, i, l, m, r, t), (b, f, i, l, n, p, s), (b, f, i, l, n, p, t), (b, f, i, l, n, q, s), (b, f, i, l, n, q, t), (b, f, i, l, n, r, s), (b, f, i, l, n, r, t), (b, f, i, l, o, p, s), (b, f, i, l, o, p, t), (b, f, i, l, o, q, s), (b, f, i, l, o, q, t), (b, f, i, l, o, r, s), (b, f, i, l, o, r, t), (c, d, g, j, m, p, s), (c, d, g, j, m, p, t), (c, d, g, j, m, q, s), (c, d, g, j, m, q, t), (c, d, g, j, m, r, s), (c, d, g, j, m, r, t), (c, d, g, j, n, p, s), (c, d, g, j, n, p, t), (c, d, g, j, n, q, s), (c, d, g, j, n, q, t), (c, d, g, j, n, r, s), (c, d, g, j, n, r, t), (c, d, g, j, o, p, s), (c, d, g, j, o, p, t), (c, d, g, j, o, q, s), (c, d, g, j, o, q, t), (c, d, g, j, o, r, s), (c, d, g, j, o, r, t), (c, d, g, k, m, p, s), (c, d, g, k, m, p, t), (c, d, g, k, m, q, s), (c, d, g, k, m, q, t), (c, d, g, k, m, r, s), (c, d, g, k, m, r, t), (c, d, g, k, n, p, s), (c, d, g, k, n, p, t), (c, d, g, k, n, q, s), (c, d, g, k, n, q, t), (c, d, g, k, n, r, s), (c, d, g, k, n, r, t), (c, d, g, k, o, p, s), (c, d, g, k, o, p, t), (c, d, g, k, o, q, s), (c, d, g, k, o, q, t), (c, d, g, k, o, r, s), (c, d, g, k, o, r, t), (c, d, g, l, m, p, s), (c, d, g, l, m, p, t), (c, d, g, l, m, q, s), (c, d, g, l, m, q, t), (c, d, g, l, m, r, s), (c, d, g, l, m, r, t), (c, d, g, l, n, p, s), (c, d, g, l, n, p, t), (c, d, g, l, n, q, s), (c, d, g, l, n, q, t), (c, d, g, l, n, r, s), (c, d, g, l, n, r, t), (c, d, g, l, o, p, s), (c, d, g, l, o, p, t), (c, d, g, l, o, q, s), (c, d, g, l, o, q, t), (c, d, g, l, o, r, s), (c, d, g, l, o, r, t), (c, d, h, j, m, p, s), (c, d, h, j, m, p, t), (c, d, h, j, m, q, s), (c, d, h, j, m, q, t), (c, d, h, j, m, r, s), (c, d, h, j, m, r, t), (c, d, h, j, n, p, s), (c, d, h, j, n, p, t), (c, d, h, j, n, q, s), (c, d, h, j, n, q, t), (c, d, h, j, n, r, s), (c, d, h, j, n, r, t), (c, d, h, j, o, p, s), (c, d, h, j, o, p, t), (c, d, h, j, o, q, s), (c, d, h, j, o, q, t), (c, d, h, j, o, r, s), (c, d, h, j, o, r, t), (c, d, h, k, m, p, s), (c, d, h, k, m, p, t), (c, d, h, k, m, q, s), (c, d, h, k, m, q, t), (c, d, h, k, m, r, s), (c, d, h, k, m, r, t), (c, d, h, k, n, p, s), (c, d, h, k, n, p, t), (c, d, h, k, n, q, s), (c, d, h, k, n, q, t), (c, d, h, k, n, r, s), (c, d, h, k, n, r, t), (c, d, h, k, o, p, s), (c, d, h, k, o, p, t), (c, d, h, k, o, q, s), (c, d, h, k, o, q, t), (c, d, h, k, o, r, s), (c, d, h, k, o, r, t), (c, d, h, l, m, p, s), (c, d, h, l, m, p, t), (c, d, h, l, m, q, s), (c, d, h, l, m, q, t), (c, d, h, l, m, r, s), (c, d, h, l, m, r, t), (c, d, h, l, n, p, s), (c, d, h, l, n, p, t), (c, d, h, l, n, q, s), (c, d, h, l, n, q, t), (c, d, h, l, n, r, s), (c, d, h, l, n, r, t), (c, d, h, l, o, p, s), (c, d, h, l, o, p, t), (c, d, h, l, o, q, s), (c, d, h, l, o, q, t), (c, d, h, l, o, r, s), (c, d, h, l, o, r, t), (c, d, i, j, m, p, s), (c, d, i, j, m, p, t), (c, d, i, j, m, q, s), (c, d, i, j, m, q, t), (c, d, i, j, m, r, s), (c, d, i, j, m, r, t), (c, d, i, j, n, p, s), (c, d, i, j, n, p, t), (c, d, i, j, n, q, s), (c, d, i, j, n, q, t), (c, d, i, j, n, r, s), (c, d, i, j, n, r, t), (c, d, i, j, o, p, s), (c, d, i, j, o, p, t), (c, d, i, j, o, q, s), (c, d, i, j, o, q, t), (c, d, i, j, o, r, s), (c, d, i, j, o, r, t), (c, d, i, k, m, p, s), (c, d, i, k, m, p, t), (c, d, i, k, m, q, s), (c, d, i, k, m, q, t), (c, d, i, k, m, r, s), (c, d, i, k, m, r, t), (c, d, i, k, n, p, s), (c, d, i, k, n, p, t), (c, d, i, k, n, q, s), (c, d, i, k, n, q, 1), (c, d, i, k, n, r, s), (c, d, i, k, n, r, t), (c, d, i, k, o, p, s), (c, d, i, k, o, p, t), (c, d, i, k, o, q, s), (c, d, i, k, o, q, t), (c, d, i, k, o, r, s), (c, d, i, k, o, r, t), (c, d, i, l, m, p, s), (c, d, i, l, m, p, t), (c, d, i, l, m, q, s), (c, d, i, l, m, q, t), (c, d, i, l, m, r, s), (c, d, i, l, m, r, t), (c, d, i, l, n, p, s), (c, d, i, l, n, p, t), (c, d, i, l, n, q, s), (c, d, i, l, n, q, t), (c, d, i, l, n, r, s), (c, d, i, l, n, r, t), (c, d, i, l, o, p, s), (c, d, i, l, o, p, t), (c, d, i, l, o, q, s), (c, d, i, l, o, q, t), (c, d, i, l, o, r, s), (c, d, i, l, o, r, t), (c, e, g, j, m, p, s), (c, e, g, j, m, p, t), (c, e, g, j, in, q, s), (c, e, g, j, m, q, t), (c, e, g, j, m, r, s), (c, e, g, j, m, r, t), (c, e, g, j, n, p, s), (c, e, g, j, n, p, t), (c, e, g, j, n, q, s), (c, e, g, j, n, q, t), (c, e, g, j, n, r, s), (c, e, g, j, n, r, t), (c, e, g, j, o, p, s), (c, e, g, j, o, p, t), (c, e, g, j, o, q, s), (c, e, g, j, o, q, t), (c, e, g, j, o, r, s), (c, e, g, j, o, r, t), (c, e, g, k, m, p, s), (c, e, g, k, m, p, t), (c, e, g, k, m, q, s), (c, e, g, k, m, q, t), (c, e, g, k, m, r, s), (c, e, g, k, m, r, t), (c, e, g, k, n, p, s), (c, e, g, k, n, p, t), (c, e, g, k, n, q, s), (C, e, g, k, n, q, t), (c, e, g, k, n, r, s), (c, e, g, k, n, r, t), (c, e, g, k, o, p, s), (c, e, g, k, o, p, t), (c, e, g, k, o, q, s), (c, e, g, k, o, q, t), (c, e, g, k, o, r, s), (c, e, g, k, o, r, t), (c, e, g, l, m, p, s), (c, e, g, l, m, p, t), (c, e, g, l, m, q, s), (c, e, g, l, m, q, t), (c, e, g, l, m, r, s), (c, e, g, l, m, r, t), (c, e, g, l, n, p, s), (c, e, g, l, n, p, t), (c, e, g, l, n, q, s), (c, e, g, l n, q, t), (c, e, g, l, n, r, s), (c, e, g, l, n, r, t), (c, e, g, l, o, p, s), (c, e, g, l, o, p, t), (c, e, g, l, o, q, s), (c, e, g, l, o, q, t), (c, e, g, l, o, r, s), (c, e, g, l, o, r, t), (c, e, h, j, m, p, s), (c, e, h, j, m, p, t), (c, e, h, j, m, q, s), (c, e, h, j, m, q, t), (c, e, h, j, m, r, s), (c, e, h, j, m, r, t), (c, e, h, j, n, p, s), (c, e, h, j, n, p, t), (c, e, h, j, n, q, s), (c, e, h, j, n, q, t), (c, e, h, j, n, r, s), (c, e, h, j, n, r, t), (c, e, h, j, o, p, s), (c, e, h, j, o, p, t), (c, e, h, j, o, q, s), (c, e, h, j, o, q, t), (c, e, h, j, o, r, s), (c, e, h, j, o, r, t), (c, e, h, k, m, p, s), (c, e, h, k, m, p, t), (c, e, h, k, m, q, s), (c, e, h, k, m, q, t), (c, e, h, k, m, r, s), (c, e, h, k, m, r, t), (c, e, h, k, n, p, s), (c, e, h, k, n, p, t), (c, e, h, k, n, q, s), (c, e, h, k, n, q, t), (c, e, h, k, n, r, s), (c, e, h, k, n, r, t), (c, e, h, k, o, p, s), (c, e, h, k, o, p, t), (c, e, h, k, o, q, s), (c, e, h, k, o, q, t), (c, e, h, k, o, r, s), (c, e, h, k, o, r, t), (c, e, h, l, m, p, s), (c, e, h, l, m, p, t), (c, e, h, l, m, q, s), (c, e, h, l, m, q, t), (c, e, h, l, m, r, s), (c, e, h, l, m, r, t), (c, e, h, l, n, p, s), (c, e, h, l, n, p, t), (c, e, h, l, n, q, s), (c, e, h, l, n, q, t), (c, e, h, l, n, r, s), (c, e, h, l, n, r, t), (c, e, h, l, o, p, s), (c, e, h, l, o, p, t), (c, e, h, l, o, q, s), (c, e, h, l, o, q, t), (c, e, h, l, o, r, s), (c, e, h, l, o, r, t), (c, e, i, j, m, p, s), (c, e, i, j, m, p, t), (c, e, i, j, m, q, s), (c, e, i, j, m, q, t), (c, e, i, j, m, r, s), (c, e, i, j, m, r, t), (c, e, i, j, n, p, s), (c, e, i, j, n, p, t), (c, e, i, j, n, q, s), (c, e, i, j, n, q, t), (c, e, i, j, n, r, s), (c, e, i, j, n, r, t), (c, e, i, j, o, p, s), (c, e, i, j, o, p, t), (c, e, i, j, o, q, s), (c, e, i, j, o, q, t), (c, e, i, j, o, r, s), (c, e, i, j, o, r, t), (c, e, i, k, m, p, s), (c, e, i, k, m, p, t), (c, e, i, k, m, q, s), (c, e, i, k, m, q, t), (c, e, i, k, m, r, s), (c, e, i, k, m, r, t), (c, e, i, k, n, p, s), (c, e, i, k, n, p, t), (c, e, i, k, n, q, s), (c, e, i, k, n, q, t), (c, e, i, k, n, r, s), (c, e, i, k, n, r, t), (c, e, i, k, o, p, s), (c, e, i, k, o, p, t), (c, e, i, k, o, q, s), (c, e, i, k, o, q, t), (c, e, i, k, o, r, s), (c, e, i, k, o, r, t), (c, e, i, l, m, p, s), (c, e, i, l, m, p, t), (c, e, i, l, m, q, s), (c, e, i, l, m, q, t), (c, e, i, l, m, r, s), (c, e, i, l, m, r, t), (c, e, i, l, n, p, s), (c, e, i, l, n, p, t), (c, e, i, l, n, q, s), (c, e, i, l, n, q, t), (c, e, i, l, n, r, s), (c, e, i, l, n, r, t), (c, e, i, l, o, p, s), (c, e, i, l, o, p, t), (c, e, i, l, o, q, s), (c, e, i, l, o, q, t), (c, e, i, l, o, r, s), (c, e, i, l, o, r, t), (c, f, g, j, m, p, s), (c, f, g, j, m, p, t), (c, f, g, j, m, q, s), (c, f, g, j, m, q, t), (c, f, g, j, m, r, s), (c, f, g, j, m, r, t), (c, f, g, j, n, p, s), (c, f, g, j, n, p, t), (c, f, g, j, n, q, s), (c, f, g, j, n, q, t), (c, f, g, j, n, r, s), (c, f, g, j, n, r, t), (c, f, g, j, o, p, s), (c, f, g, j, o, p, t), (c, f, g, j, o, q, s), (c, f, g, j, o, q, t), (c f, g, j, o, r, s), (c, f, g, j, o, r, t), (c, f, g, k, m, p, s), (c, f, g, k, m, p, t), (c, f, g, k, m, q, s), (c, f, g, k, m, q, t), (c, f, g, k, m, r, s), (c, f, g, k, m, r, t), (c, f, g, k, n, p, s), (c, f, g, k, n, p, t), (c, f, g, k, n, q, s), (c, f, g, k, n, q, t), (c, f, g, k, n, r, s), (c, f, g, k, n, r, t), (c, f, g, k, o, p, s), (c, f, g, k, o, p, t), (c, f, g, k, o, q, s), (c, f, g, k, o, q, t), (c, f, g, k, o, r, s), (c, f, g, k, o, r, t), (c, f, g, l, m, p, s), (c, f, g, l, m, p, t), (c, f, g, l, m, q, s), (c, f, g, l, m, q, t), (c, f, g, l, m, r, s), (c, f, g, l, m, r, t), (c, f, g, l, n, p, s), (c, f, g, l, n, p, t), (c, f, g, l, n, q, s), (c, f, g, l, n, q, t), (c, f, g, l, n, r, s), (c, f, g, l, n, r, t), (c, f, g, l, o, p, s), (c, f, g, l, o, p, t), (c, f, g, l, o, q, s), (c, f, g, l, o, q, t), (c, f, g, o, r, s), (c, f, g, o, r, t), (c, f, h, j, m, p, s), (c, f, h, j, m, p, t), (c, f, h, j, m, q, s), (c, f, h, j, m, q, t), (c, f, h, j, m, r, s), (c, f, h, j, m, r, t), (c, f, h, j, n, p, s), (c, f, h, j, n, p, t), (c, f, h, j, n, q, s), (c, f, h, j, n, q, t), (c, f, h, j, n, r, s), (c, f, h, j, n, r, t), (c, f, h, j, o, p, s), (c, f, h, j, o, p, t), (c. f, h, j, o, q, s), (c, f, h, j, o, q, t), (c, f, h, j, o, r, s), (c, f, h, j, o, r, t), (c, f, h, k, m, p, s), (c, f, h, k, m, p, t), (c, f, h, k, m, q, s), (c, f, h, k, m, q, t), (c, f, h, k, m, r, s), (c, f, h, k, m, r, t), (c, f, h, k, n, p, s), (c, f, h, k, n, p, t), (c, f, h, k, n, q, s), (c, f, h, k, n, q, t), (c, f, h, k, n, r, s), (c, f, h, k, n, r, t), (c, f, h, k, o, p, s), (c, f, h, k, o, p, t), (c, f, h, k, o, q, s), (c, f, h, k, o, q, t), (c, f, h, k, o, r, s), (c, f, h, k, o, r, t), (c, f, h, l, m, p, s), (c, f, h, l, m, p, t), (c, f, h, l, m, q, s), (c, f, h, l, m, q, t), (c, f, h, l, m, r, s), (c, f, h, l, m, r, t), (c, f, h, l, n, p, s), (c, f, h, l, n, p, t), (c, f, h, l, n, q, s), (c, f, h, l, n, q, t), (c, f, h, l, n, r, s), (c, f, h, l, n, r, t), (c, f, h, l, o, p, s), (c, f, h, l, o, p, t), (c, f, h, l, o, q, s), (c, f, h, l, o, q, t), (c, f, h, l, o, r, s), (c, f, h, l, o, r, t), (c, f, i, j, m, p, s), (c, f, i, j, m, p, t), (c, f, i, j, m, q, s), (c, f, i, j, m, q, t), (c, f, i, j, m, r, s), (c, f, i, j, m, r, t), (c, f, i, j, n, p, s), (c, f, i, j, n, p, t), (c, f, i, j, n, q, s), (c, f, i, j, n, q, t), (c, f, i, j, n, r, s), (c, f, i, j, n, r, t), (c, f, i, j, o, p, s), (c, f, i, j, o, p, t), (c, f, i, j, o, q, s), (c, f, i, j, o, q, t), (c, f, i, j, o, r, s), (c, f, i, j, o, r, t), (c, f, i, k, m, p, s), (c, f, i, k, m, p, t), (c, f, i, k, m, q, s), (c, f, i, k, m, q, t), (c, f, i, k, m, r, s), (c, f, i, k, m, r, t), (c, f, i, k, n, p, s), (c, f, i, k, n, p, t), (c, f, i, k, n, q, s), (c, f, i, k, n, q, t), (c, f, i, k, n, r, s), (c, f, i, k, n, r, t), (c, f, i, k, o, p, s), (c, f, i, k, o, p, t), (c, f, i, k, o, q, s), (c, f, i, k, o, q, t), (c, f, i, k, o, r, s), (c, f, i, k, o, r, t), (c, f, i, l, m, p, s), (c, f, i, l, m, p, t), (c, f, i, l, m, q, s), (c, f, i, l, m, q, t), (c, f, i, l, m, r, s), (c, f, i, l, m, r, t), (c, f, i, l, n, p, s), (c, f, i, l, n, p, t), (c, f, i, l, n, q, s), (c, f, i, l, n, q, t), (c, f, i, l, n, r, s), (c, f, i, l, n, r, t), (c, f, i, l, o, p, s), (c, f, i, l, o, p, t), (c, f, i, l, o, q, s), (c, f, i, l, o, q, t), (c, f, i, l, o, r, s), (c, f, i, l, o, r, t).

The present invention tablet has excellent light-stability as shown in the examples mentioned later. In spite of high content of the main ingredient, the tablet is compact, sufficiently hard and readily administrable.

The dosage varies with the conditions of the patients, administration route, their age, and body weight. In the case of oral administration, the dosage is thought to be preferable between about 1200 mg to about 1800 mg per a day. The amount per one administration is between 400 mg to 600 mg because of three division a day, and it is preferable to take two tablets each containing the main ingredient of between 200 mg to 300 mg.

The following examples and test examples are provided to further illustrate the present invention and are not to be construed as limiting the scope thereof.

Example

Example 1

Preparation of Pirfenidone Tablets

Pirfenidone (2,000 g) was mixed with 560 g of lactose and 50 g of carmellose calcium. The mixture was granulated by spraying a 5 (W/W) % aqueous solution of hydroxypropylcellulose (60 g) with a fluid bed granulator. Carmellose calcium and magnesium stearate were added to the granules at the ratios of 5.6 and 1.1 wt. % to the weight of the granules, respectively. The obtained mixture was compressed at a force of 13 kN and to give plain pirfenidone tablets each containing 200 mg of pirfenidone (size: 12.0×6.0 mm, weight: 285 mg/tablet).

The plain tablets were coated by spraying a 10 wt. % aqueous solution containing hydroxypropylmethylcellulose (66.7 g), triethyl citrate (6.7 g), and titanium oxide 26.6 g in an amount of 10 mg per tablet with a High-coator, to give the objective pirfenidone tablets.

The components of a pirfenidone tablet is shown below.

TABLE 1

| Component | Amount | Note |
| --- | --- | --- |
| Pirfenidone | 200.0 mg | |
| Lactose | 56.0 mg | |
| Carmellose calcium | 20.0 mg | Intra-granular: 5.0 mg Extera-granular 15.0 mg |
| Hydroxypropylcellulose | 6.0 mg | |
| Magnesium stearate | 3.0 mg | |
| Total of weight of a plain tablet | 285.0 mg | |
| Hydroxypropylmethylcellulose 2910 | 6.67 mg | |
| Titanium oxide | 2.66 mg | |
| Triethyl citrate | 0.67 mg | |
| Magnesium stearate | trace | 0.02 mg |
| Talc | trace | 0.02 mg |
| Total weight of coating | 10.00 mg | |
| Total weight of a coated tablet | 295.0 mg | |

Example 2

Light Exposure Testing

Light exposure test of pirfenidone was carried out under the following condition, using "drug substance" obtained by packing 500 mg of milled pirfenidone drug substance in a heat-sealed transparent SP (Striped Package), "compressed drug substance" obtained by statically compressing 300 mg of milled pirfenidone drug substance, "the plain tablets" obtained in the above Example 1, and "the coated tablets" obtained in the above Example 1. The results are shown in table 2.

(Test Condition)

light irradiation apparatus: light stability test apparatus (LTL400-D5) (Nagano Science Equipment Mfg. Co., Ltd.)

fluorescent light: D65 fluorescent lamp for color comparing and test temperature and humidity: 25° C., room humidity illumination intensity: 3570 Lx exposure dose: 1,200,000 Lx·hr coloring difference measure apparatus: Color analyzer TC-1800MK-II measurement method: reflected ray measurement color specification system: CIELAB measurement condition: second degree visual field standard light: C

TABLE 2

| Sample | Color difference (ΔE) | Discoloration |
|---|---|---|
| Drug substance | 0.73 | slight |
| Compressed drug substance | 3.62 | remarkable |
| Plain tablets | 5.08 | remarkable |
| Coated tablets | 0.75 | slight |

Table 2 showed that remarkable color difference was not observed in the case of the pirfenidone drug substance, but a pirfenidone compressed drug substance and a pirfenidone plain tablet have a problem in light-stability. However, a pirfenidone coated tablet solves the problem in light-stability. A pirfenidone coated tablet is confirmed to have no problem in odor or bitterness.

INDUSTRIAL APPLICABILITY

The present invention provides a compact and sufficiently hard tablet containing a high content of pirfenidone which is necessary to be administered in high dose. And at the same time, the present invention solves the problem of its odor or bitterness and provides a readily administrable tablet. Furthermore, it solves the problem of light-stability caused by tableting pirfenidone and provides the stability requested as a medicine.

The invention claimed is:

1. A tablet comprising a tablet core comprising 200 mg 5-methyl-1-phenyl-2-(1H)-pyridone, 56 mg lactose, 20 mg carmellose calcium, 6.0 mg hydroxypropylcellulose, 3 mg magnesium stearate, and a coating layer comprising 6.67 mg hydroxypropylmethylcellulose, 0.67 mg triethyl citrate, and 2.66 mg titanium oxide; wherein the tablet core is a compressed tablet and the coating layer coats the tablet core.

* * * * *